(12) United States Patent
Merkl et al.

(10) Patent No.: US 9,008,414 B2
(45) Date of Patent: Apr. 14, 2015

(54) METHOD AND APPARATUS FOR ASSISTED TRAJECTORY PLANNING

(75) Inventors: Brandon Merkl, Erie, CO (US); Rasool Khadem, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 519 days.

(21) Appl. No.: 13/252,683

(22) Filed: Oct. 4, 2011

(65) Prior Publication Data

US 2013/0085344 A1 Apr. 4, 2013

(51) Int. Cl.
G06K 9/62 (2006.01)
G06F 19/00 (2011.01)
A61B 19/00 (2006.01)

(52) U.S. Cl.
CPC .......... *G06F 19/3437* (2013.01); *A61B 19/50* (2013.01); *A61B 19/5244* (2013.01); *A61B 2019/507* (2013.01)

(58) Field of Classification Search
None
See application file for complete search history.

(56) References Cited

U.S. PATENT DOCUMENTS

| | | | |
|---|---|---|---|
| 5,592,939 A | 1/1997 | Martinelli | |
| 5,913,820 A | 6/1999 | Bladen et al. | |
| 5,983,126 A | 11/1999 | Wittkampf | |
| 6,474,341 B1 | 11/2002 | Hunter et al. | |
| 6,747,539 B1 | 6/2004 | Martinelli | |
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,313,430 B2 * | 12/2007 | Urquhart et al. | 600/429 |
| 7,751,865 B2 | 7/2010 | Jascob et al. | |
| 7,797,032 B2 | 9/2010 | Martinelli et al. | |
| 7,803,164 B2 * | 9/2010 | Gielen et al. | 606/130 |
| 8,150,497 B2 * | 4/2012 | Gielen et al. | 600/427 |
| 8,315,689 B2 * | 11/2012 | Jenkins et al. | 600/410 |
| 2004/0116803 A1 | 6/2004 | Jascob et al. | |
| 2004/0199072 A1 | 10/2004 | Sprouse et al. | |
| 2007/0249911 A1 | 10/2007 | Simon | |
| 2008/0064947 A1 | 3/2008 | Heruth et al. | |
| 2008/0081982 A1 | 4/2008 | Simon et al. | |
| 2008/0123922 A1 | 5/2008 | Gielen et al. | |
| 2008/0123923 A1 | 5/2008 | Gielen et al. | |

(Continued)

FOREIGN PATENT DOCUMENTS

WO WO-2008039243 A1 4/2008

OTHER PUBLICATIONS

Dracopoulos D C: "robot path planning for maze navigation", Neural Networks Proceedings, 1998. IEEE World Congress on Computationa L Intelligence. The 1998 IEEE International Joint Conference on Anchorage, AK, USA May 4-9, 1998, New York, NY, USA, IEEE, US, vol. 3, May 4, 1998, pp. 2081-2085.

(Continued)

*Primary Examiner* — Vikkram Bali
(74) *Attorney, Agent, or Firm* — Harness, Dickey

(57) ABSTRACT

A procedure can be assisted by a processor system, such as a computer system. A trajectory can be used to identify a selected trajectory or path of an instrument to reach a tumor within a brain of a subject, reach a selected portion of the anatomy (e.g. sub-thalamic nucleus (STN) or spinal cord), or other appropriate target. The planning algorithm can include both inputted data and learned rankings or ratings related to selected trajectories. The planning algorithm can used the learned ratings to rate and later determined trajectories.

22 Claims, 7 Drawing Sheets

(56) References Cited

U.S. PATENT DOCUMENTS

| | | | |
|---|---|---|---|
| 2009/0259230 A1* | 10/2009 | Khadem et al. | 606/130 |
| 2010/0228117 A1 | 9/2010 | Hartmann | |
| 2010/0274311 A1 | 10/2010 | Vaidyanathan et al. | |
| 2012/0184844 A1* | 7/2012 | Gielen et al. | 600/424 |

OTHER PUBLICATIONS

Essert C. et al.: "Automatic computation of electrode trajectories for Deep Brain Stimulation: a hybrid symbolic and numerical approach", International Journal of Computer assisted Radiology and Surgery 2012 Springer Verlag Deu, vol. 7, No. 4. Aug. 25, 2011, pp. 517-532, XP002692317, ISSN: 1861-6410.

International Search Report and Written Opinion for PCT/US2012/058438 mailed Mar. 7, 2013, claiming benefit of U.S. Appl. No. 13/252,683, filed Oct. 4, 2011.

"Mayfield® Skull Clamps and Headrest Systems," Mayfield® Surgical Devices Product Index, pp. 1-6, Dec. 2004 Integra LifeSciences Corporation.

"Medtronic O-Arm Multi-Dimensional Surgical Imaging System"; Brochure, 24pp, 2009.

"StealthStation_S7_System® Information Center in the OR," (2009) Medtronic, Inc.

"StealthStation® TRIA™ plus Treatment Guidance System," brochure, Medtronic Surgical Navigation Technologies (2004) 2 pages.

"TREON, StealthStation," brochure, Medtronic Surgical Navigation Technologies (2001) 8 pages.

"AxiEM Electromagetic Navigation," tri-fold brochure, Medtronic Navigation (2005) 2 pages.

International Preliminary Report on Patentability and Written Opinion for PCT/US2012/058438 mailed Apr. 17, 2014, claiming benefit of U.S. Appl. No. 13/252,683, filed Oct. 4, 2011.

* cited by examiner

METHOD AND APPARATUS FOR ASSISTED TRAJECTORY PLANNING

FIELD

The subject disclosure relates to assisted surgical procedures, and particularly to system training for assisting in or rating procedures.

BACKGROUND

This section provides background information related to the present disclosure which is not necessarily prior art.

Procedures can be performed on various structures, such as a human anatomy or other animal anatomies. The procedures, however, may generally be either open procedures or closed or less invasive procedures. In an open procedure, the anatomy of the patient or subject is open for viewing by a surgeon. In a less invasive procedure, however, it can be selected to minimize the access or viewing of the internal portions of the subject. It may be selected, therefore, to use imaging to assist in performing a less invasive procedure.

Images of the subject can be used to assist in performing a procedure by illustrating the internal structure of the subject. Various tracking and navigation systems can be used to assist in locating and illustrating the location of the instrument relative to the structure by displaying an icon relative to the image. For example, an icon representing an instrument can be super-imposed on the image of the structure of the subject to illustrate the location of the instrument relative to the subject.

The instrument can be passed through the subject at various entry locations, angles, and depths relative to the subject. These various features can be defined as a trajectory which includes an entry point and a path of the instrument from the entry point to a selected target. The trajectory may also be defined by any appropriate geometric shape, such as cones, regular or irregular volume shapes, cylinders, etc. A surgeon or other appropriate user can identify a trajectory to reach a target that is to be followed during an actual procedure. Accordingly, image data of the subject can be acquired prior to performing a procedure and the procedure can be planned with the image data to assist in defining an appropriate trajectory to the target.

SUMMARY

This section provides a general summary of the disclosure, and is not a comprehensive disclosure of its full scope or all of its features.

An assisted procedure can be assisted by a computer system. The computer system can include an appropriate processor (e.g. processing cores provided by corporations such as Intel Corporation or Advanced Micro Devices) or processing system that can execute instructions based on a trained algorithm to assist in solving or identifying a problem. For example, a procedure or algorithm can be used to assist in planning a trajectory to perform a procedure. A trajectory can be used to identify a path of an instrument to reach a tumor within a brain of a subject, reach a selected portion of the anatomy (e.g. sub-thalamic nucleus (STN) or spinal cord), or other appropriate targets. The trained algorithm can include both inputted data and learned rankings or ratings related to selected trajectories to assist in determining and displaying a trajectory for a selected procedure. The trained algorithm can also include information or data related to previously performed surgeries, case studies from literature or provided by selected surgeons, or ratings or rankings of trajectories deemed safe, efficacious, or appropriate from any appropriate source. For example, an assisted trajectory planning (ATP) system can include both learned coefficients from ratings based upon previously performed (also referred to as training datasets) procedures. Online or onsite training can use later acquired or clinical datasets of a user or clinician. Also, datasets can include current subject datasets which can be for a subject for which a procedure is to be rated and/or performed. Using ratings of previously performed procedures can be referred to as offline or prior training. The training based upon current clinician procedures ratings can be referred to as online training. Regardless of the training, the system can use ratings of selected trajectories to assist in identifying features to determine coefficients to propose ratings of selected trajectories for use by a user. Additionally, the online training can be used to assist in personalizing or specifying ratings for a particular clinician (such as a surgeon) based upon the on-line or active training. Additionally, the online training can include sampling and/or resampling data from various performed procedures for learning coefficients to new targets. For example, bootstrapping regression, jack-knifing, cross-validation, randomization tests, and permutation tests can be used to analyze and test data to determine coefficients for selected targets not previously within the algorithms range.

Accordingly, the ATP system can be used to provide a generic rating system that can be augmented on site or online by a clinician to assist in minimizing variances between ratings of various trajectories given based on the ATP system and ratings that would be applied by the particular clinician.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The subject disclosure relates generally to performing a procedure on a subject, which can include a human subject. It will be understood, however, that the subject can include any appropriate subject where a procedure can be planned to move an instrument from an exterior of the subject into an interior of the subject. The subject can include various animate or inanimate objects. For example, it can be selected to move an instrument from exterior to a shell or casing of an automotive or electronic system without removing large portions to reach the internal portions. Images of the selected subject's system can be acquired and trajectories can be planned to move an instrument from the exterior to the interior of the subject to perform a function, such as repair or removal of a selected component within the inanimate object. Accordingly, it will be understood that the subject disclosure is not limited to performing a procedure on a human anatomy, but rather that the subject disclosure is related generally to a procedure, including training a planning system, and performing a procedure with assistance of the planning system or the assisted trajectory planning (ATP) system on any appropriate subject.

Figure 1:
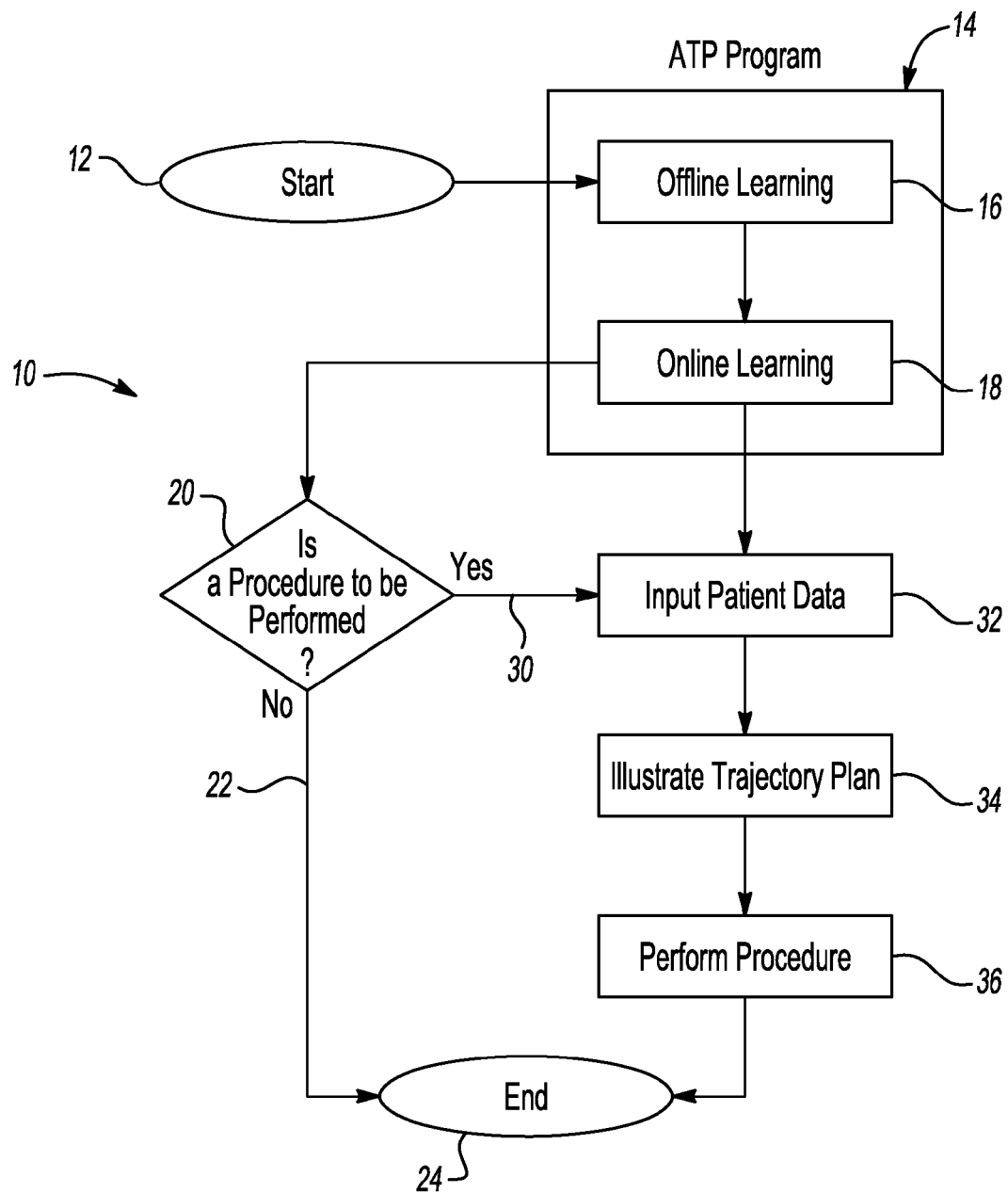
FIG. 1 is an overview of a planning algorithm and procedure.
Figure 2:
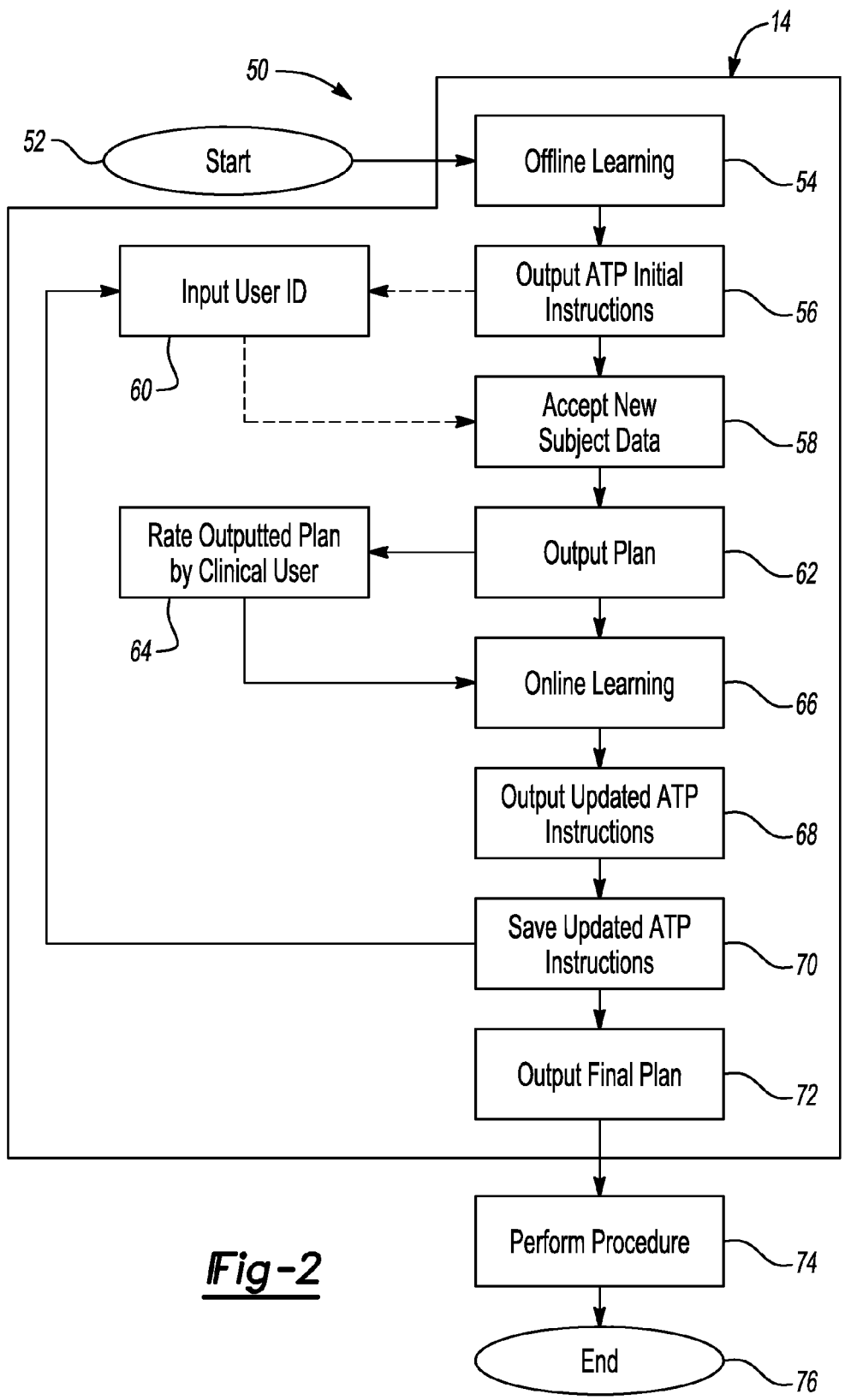
FIG. 2 is an overview plan of a clinical application of the planning algorithm.
Figure 3:
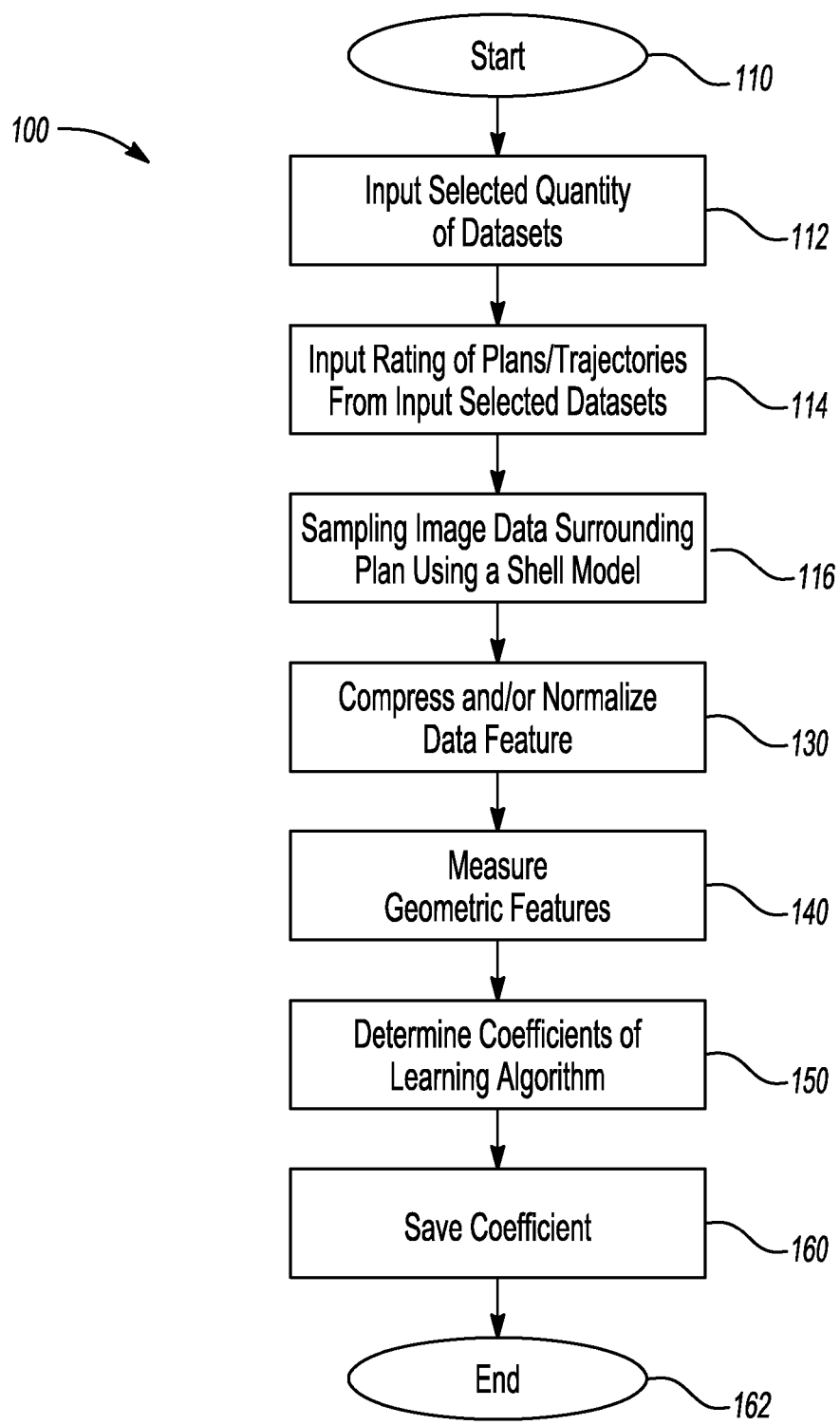
FIG. 3 is a flowchart regarding offline learning.
Figure 6:
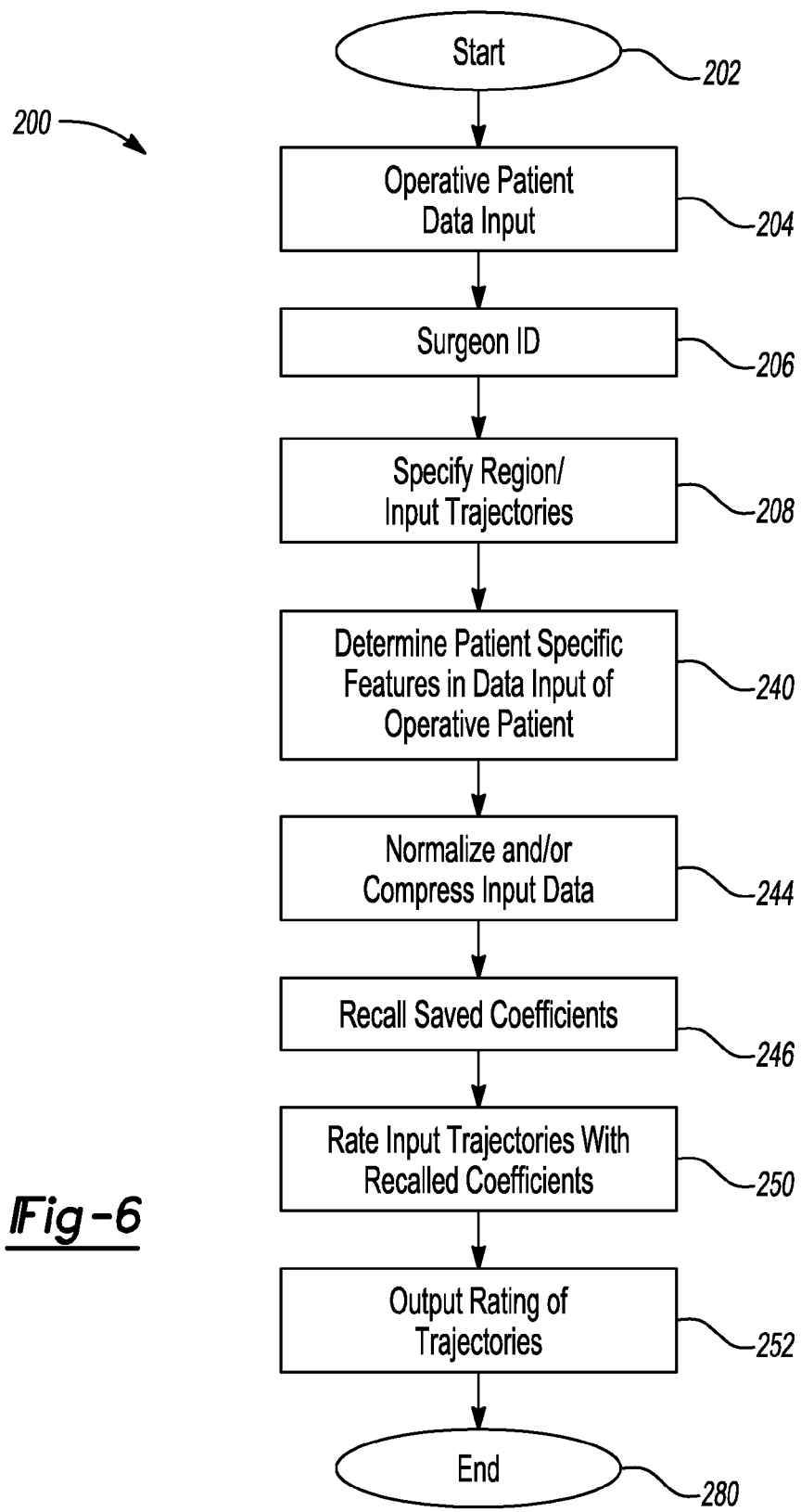
FIG. 6 is a flowchart of a use of a rating algorithm according to various embodiments of the subject disclosure.
Figure 8:
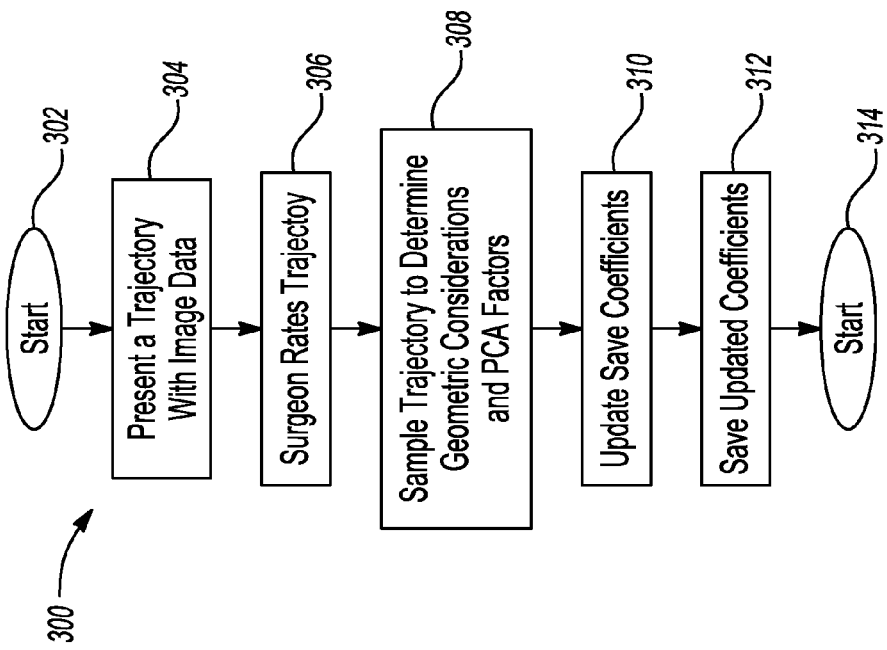
FIG. 8 is a flowchart of an online learning portion of the learning algorithm, according to various embodiments.

With reference to FIG. 1, a general overview flowchart 10 of training an ATP system and performing a procedure with an ATP system is illustrated. The overview flowchart 10 illustrated in FIG. 1 illustrates a very broad view of a system as herein discussed. Generally the flowchart 10 illustrates and describes a generation of an ATP system and a use thereof. With reference to FIG. 2 an exemplary use of the broad system 10 is illustrated. FIGS. 3, 6, and 8 illustrate in greater detail various portions of the system discussed in FIGS. 1 and 2.

With initial reference to FIG. 1, the ATP system and procedure according to the flow chart 10 can begin in START block 12. Once the procedure is started, the procedure can proceed into an assisted trajectory procedure (ATP) program 14. The ATP program 14 can include or be trained with both an offline learning feature in block 16 and an online learning feature in block 18. The ATP program 14, however, need not include both offline learning 16 and online learning 18. As discussed herein, the offline learning portion in block 16 (exemplarily illustrated in flowchart 100 in FIG. 3) can include a system or procedure that allows training the ATP learning program 14 using prior acquired data (also referred to as training datasets) and/or a plurality of inputs (also referred to as training ratings) from a plurality of experts (e.g. surgeons). The online learning portion in block 18 (exemplarily illustrated in flowchart 200 in FIG. 6) can include an as-performed or sequentially updated training of the ATP learning program 14 or saved portion thereof. It will be understood, therefore, that the online learning portion 18 can include acquiring data or inputting data while performing an actual procedure on a selected subject, but does not require a subject to be selected but an rather include simply additional training after the offline learning in block 16.

Once the ATP learning program 14 is implemented or trained, a determination of whether a procedure is to be performed is made in decision block 20. If no procedure is to be performed, a NO path 22 can be followed to an END block 24. However, if a procedure is to be performed, the YES path 30 can be followed.

When a procedure is to be performed, the YES path 30 is followed to input patient data in block 32. The patient data inputted in block 32 can be any appropriate patient data including the patient data that is inputted for the offline learning in block 16. The offline learning procedure in block 16 and the online learning procedure in block 18 will be discussed in further detail as will the discussion of appropriate or selected patient data (e.g. diagnosis, gender, etc.). It will be understood that patient data inputted in block 32 need not be every type of patient data that is used in the offline learning in block 16, but rather can be any appropriate, selected, or obtained patient data.

After the patient data is inputted in block 32, a trajectory plan can be illustrated in block 34. As also discussed further herein, the trajectory plan can be illustrated as an icon superimposed on image data of a selected subject including an entry point, instrument path, and target. Accordingly, once the patient data is inputted in block 32, the ATP program 14 can output one or more selected trajectories and/or ratings of one or more selected trajectories and the trajectories and/or the ratings can be illustrated in block 34. The illustrated trajectory in block 34 can then be used to perform a procedure in block 36. Alternatively, or in addition thereto, other trajectories can be determined and rated.

In performing the procedure in block 36, it will be understood that any appropriate procedure can be performed based on the input patient data. For example, if the input patient data includes the location of a tumor the performed procedure can include following a trajectory illustrate in block 34 to remove the tumor. Alternatively, it will be understood that the procedure can include a placement of pedicle screws, placement of deep brain stimulation (DBS) probes, or other appropriate procedures. Once the procedure is performed in block 36, the ATP system can end in block 24.

The procedure illustrated in FIG. 1, generally includes a broad overview of the ATP program in block 14 and performing a procedure in block 36 based thereon. It will be understood, however, that the ATP program 14 can be used to perform a procedure after being implemented by a selected user, and the ATP program 14 can continue to learn from the user in the online learning portion in block 18.

With reference to FIG. 2, an example of the procedure in flowchart 10 is illustrated as a clinical application procedure in flowchart 50. Generally, the procedure can start in START block 52. The procedure can then proceed into the ATP 14, including to offline learning in block 54 which is similar or identical to the offline learning 16 in FIG. 1. The offline learning, as discussed further herein, can include training a learning algorithm, including the ATP program 14, based upon inputs and data from a plurality of training datasets from or based on selected patients and/or cases. For example, expert raters (e.g. selected surgeons, practitioners, etc.) can be selected to rate various procedures and the algorithm can learn how to rate further or additionally inputted procedures. Once appropriate learning is achieved in the offline learning in block 54, an output of ATP initial instructions can be performed in block 56. The output ATP initial instructions in block 56 can generally be understood to be a software package that can be distributed for various users or clinicians.

After the output ATP initial instructions (also referred to as learned coefficients) 56 are loaded on selected systems, such as a computer system or processor system (e.g. the processor system 500 in FIG. 9) that can include a selected processor for executing instructions, new subject data can be accepted or input in block 58. The new subject data accepted in block 58 can be data that relates to any subject other than the subjects or at least the particular data inputted for the offline learning in block 54. It will be understood also that the continued or online learning can be substantially user specific, therefore it can be selected to input a user I.D. in block 60 either prior to, consecutively or concurrently with new subject data, or after accepting new subject data. User specific capturing can be specific to a rating for a selected target, metric (e.g. safety, efficacy, etc.), or other user specific selection.

Figure 9:
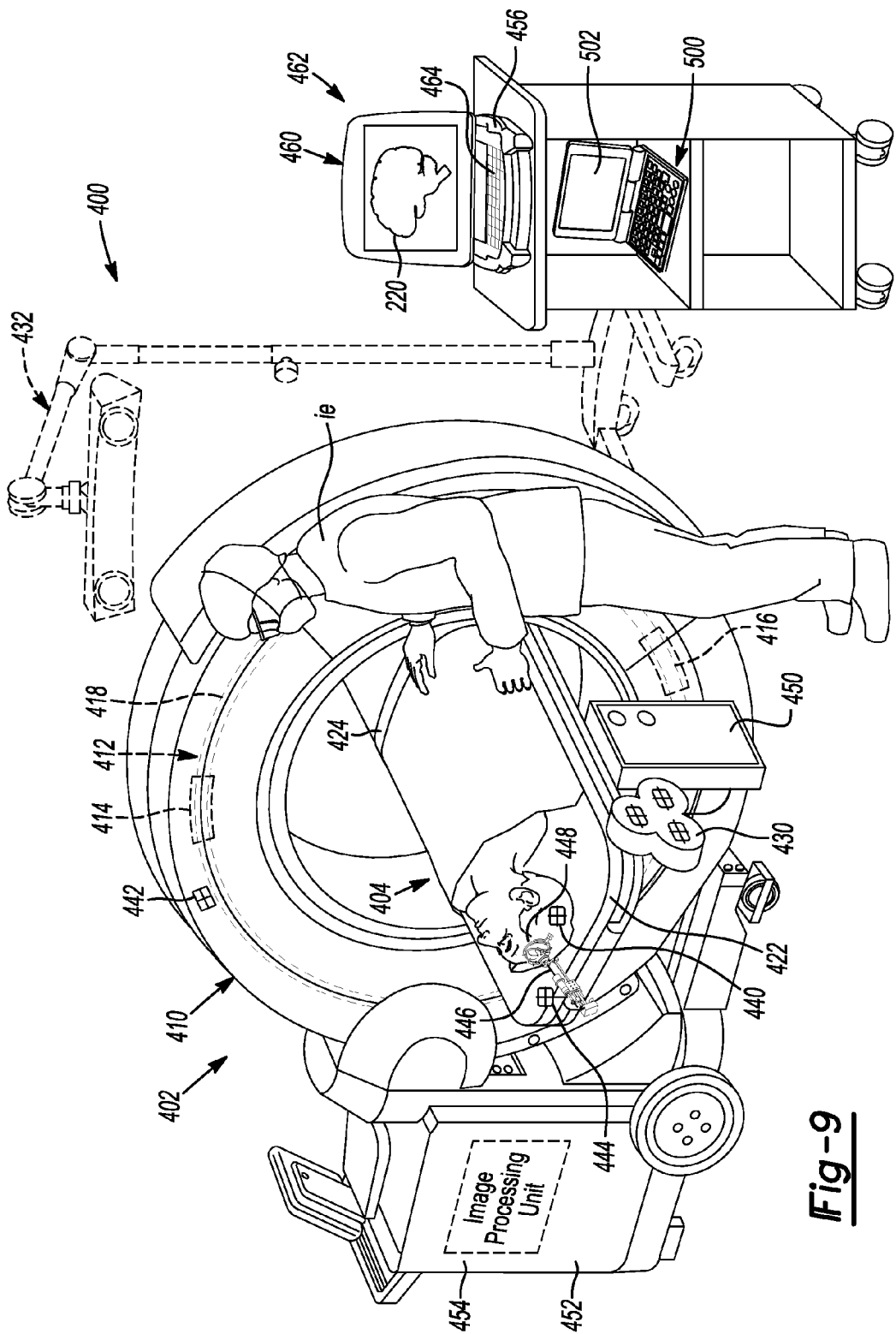
FIG. 9 is an environmental diagram of a planning and navigation system for assisting in planning and/or performing a procedure, according to various embodiments.

After accepting new subject data, a plan can be output in block 62 based upon the outputted ATP initial instructions in block 56. The outputted plan can include a rating determined by the ATP initial instructions from block 56 and can then be rated in block 64 by a clinical user or consumer who was identified in block 60. Generally, the clinical user is a user using the ATP system 14 to plan or perform a procedure on a selected subject, as illustrated in FIG. 9. The rating can be any appropriate rating by the user and can be based upon the user's experience, patient condition, or the like. The clinical user is separate from the selected expert raters used in the offline learning in block 54. The rating of the outputted plan can be used in an online learning 66 (similar or identical to the online learning 18), which can be used to further teach the ATP system 14. Accordingly, the ATP instructions can be updated and output updated ATP instructions can be made in block 68.

The outputted updated ATP instructions can be saved in block 70. The outputted saved ATP instructions can then be used to further analyze the accepted new subject data in block 58. Also, the user I.D. can again be queried to ensure that the same user that caused the outputted updated ATP instructions to be saved is also using the system. As discussed further herein, the online learning can assist in determining updated ATP instructions that are user specific, thus querying the user I.D. can ensure that the appropriate instructions are used for the plan rating by the ATP system 14.

Figure 7:
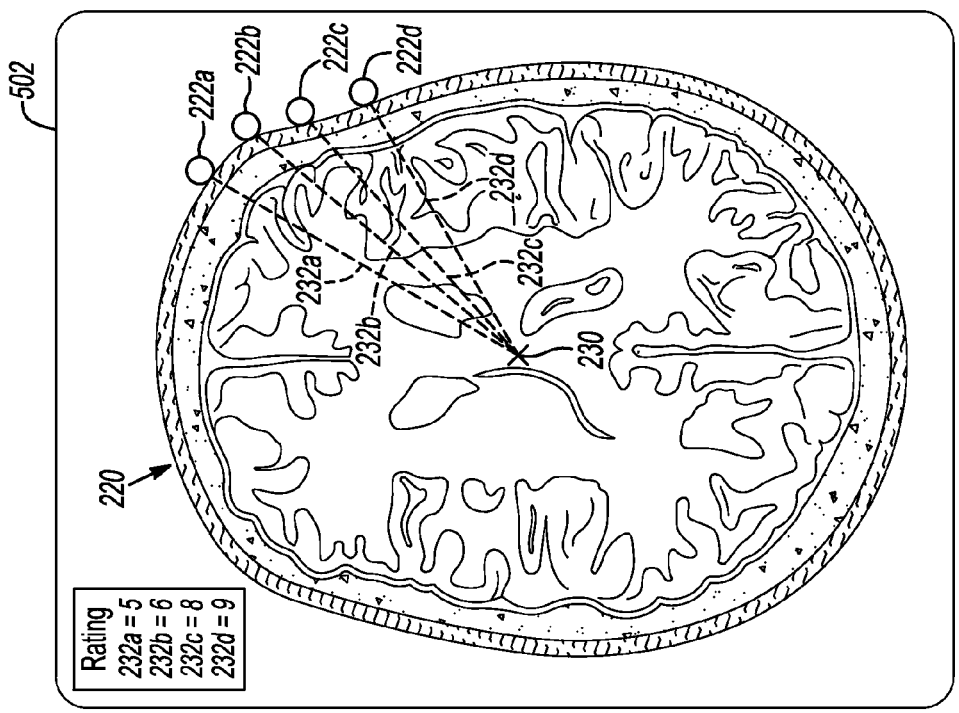
FIG. 7 is a display of an output of the rating algorithm, according to various embodiments of the subject disclosure.

A final plan can then be outputted in block 72 that is based upon the saved updated ATP instructions and accepted by the clinical user. The final plan from block 72 can also include a plan or trajectory that is constrained by a final score against one or more metrics (e.g. efficacy, safety, etc.). The final plan may alternatively or also be constrained by entrypoint or region defined by a user, or can include an output of all acceptable plans in graphical or textual form. For example, as illustrated in FIG. 7, a plurality of plans may be illustrated if selected by a user and the plurality of plans can be a graphical output as the final plan.

Upon acceptance of a trajectory from the ATP system 14, a procedure can then be performed in block 74 based upon the outputted final plan and the procedure can end in block 76. Thus, the ATP learning system can then be used to identify appropriate trajectories and can be altered based upon user input to further teach the algorithm to assist in identifying or rating trajectories for the user. This can assist in providing user specific trajectories and trajectories or ratings that will be more readily accepted by a particular user based upon the instructions. Nevertheless, the algorithm can use the initial or offline learning to assist in analyzing and rating trajectories for the user in the initial output plan in block 62 when used in a new or subsequent procedure.

The ATP system can be a learning system as briefly discussed above, and discussed in further detail herein. The various learning can include both offline learning using original or initial data, as briefly discussed above, and also further discussed further herein. The data can be analyzed and used to provide trajectories or suggest trajectories that are rated by selected users to assist in providing a baseline or initial ATP system that can be used to rate new trajectories. Accordingly, the offline learning can initially train the ATP system. The online learning, as also discussed further herein, can be used to customize and enhance the rating based on a specific clinical user. For example, a specific user may prefer or rate a certain type of plan (e.g. a straight as opposed to a curved trajectory) better or worse. Thus, the online learning can assist in speeding in selecting a trajectory acceptable to a particular condition and/or user.

With reference to FIG. 3, an offline learning process 100 is illustrated. The offline learning process 100 can include training an algorithm, as discussed further herein, to assist in performing or determining at least ratings (e.g. better or worse or more or less preferred) of trajectory plans. As discussed above, offline learning can include offline learning in block 16 or block 54, according to the selected procedure. As discussed above, generally, offline learning includes selected expert raters that have rated plans in training data sets. Accordingly, offline learning can start in block 110. Regardless, the offline learning 100 is used to train a learning algorithm to rate plans including trajectories for selected procedures. Procedures can include surgical procedures, such as tumor removal or DBS placement.

The offline learning 100 can then input a selected quantity of datasets in block 112. The datasets inputted in block 112 can include appropriate data or various specific data points. For example, a dataset can include image data (including images of a subject, such as a patient 404, FIG. 9) and information relating to a particular patient for a particular procedure. As a specific example, performing a procedure can include moving a deep brain stimulation (DBS) probe to a sub-thalamic nucleus (STN). The selected dataset, therefore, can include information relating to the specific procedure on a patient and specific data of the patient (e.g. image data). For example, a single selected patient X can have a dataset that can include various information relating to patient X. The patient and the single procedure relating to the patient X can include image data relating to the patient. In the example of placing a DBS in a brain that dataset can include image data of a brain. The image data can include magnetic resonance imaging (MRI) data, computed tomography (CT) data or other appropriate image data. The image data can be only a portion of the dataset. Additionally, data can include a plan, either preplanned or performed and can include a trajectory of an instrument for placing the DBS within the brain of patient X. The plan can include an actual plan performed on the patient X or a plan for performing a procedure on patient X. Accordingly, the plan can include identifying various portions of the image data, such as an anterior commissure (AC) and a posterior commissure (PC) in the image data. Additionally, the plan can include an identified target point (e.g. a point within the STN) and an entry point. The entry point can then be a point through which the instrument will pass to enter into the brain of the patient. The entry point can be on the skin of the patient, the skull bone of the patient, or any other appropriate entry point. The particular dataset can also include specific information relating to the patient X. Patient X specific information can include demographic data such as an age of patient X, a gender of patient X, or other patient specific information. Patient specific information can further include previous procedures that have been performed on patient X, other conditions of patient X, or the like. Additionally, datasets can include information relating to the clinician performing the procedure. For example, as discussed further herein, the ATP can be specialized for a particular clinician. Accordingly, an I.D. of a surgeon or clinician can be entered as a part of the dataset.

A plurality or selected quantity of training datasets can be acquired for input in block 112. The training datasets can be from a selected population or sample thereof (e.g. selected number of prior patients or selected patients) to train the ATP system. For each of the training datasets an input of a rating for the plan can be inputted by a selected rater in block 114. For example, in the initial offline learning procedure, selected practitioners or expert raters can be selected to rate the training dataset that include plans. Each dataset includes a plan, either one based upon a preplanned procedure or a plan based upon a performed procedure, and the plan can be rated by an expert.

The rating can be any appropriate rating system, in block 114, for example a rating of 1-10 where a rating of 10 can be a plan that is identified as substantially perfect by the rating individual or 1 refers to a plan that includes extreme hazard or is substantially undesirable by the selected rater. Accordingly, the selected expert or practitioner (herein also referred to as a rater) can rate in block 114 each of the plans from the input dataset from block 112. It is understood that any appropriate coding can be used to rate at least plans or trajectories used in the training datasets.

The particular rater can rate every dataset input in block 112 to provide a complete set of ratings based upon the individual rater. A plurality of plans or trajectories can be rated for each dataset. Each dataset, however, can be specific to a particular plan where a particular plan can include a single trajectory having an entry point and a target within a selected region that can be rated by the rater. Accordingly, a plurality of datasets can be rated by the raters in block 114 to provide a plurality of ratings regarding a plurality of datasets that are input in block 112 to provide information of ratings of a plurality of trajectories based on a plurality of input datasets.

Figure 4:
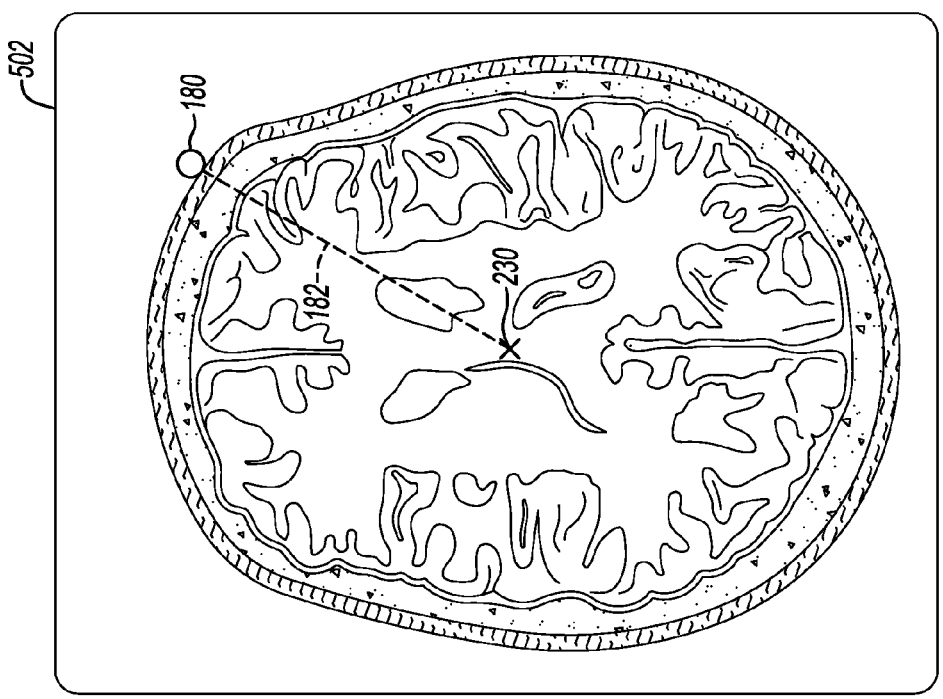
FIG. 4 is an exemplary illustration of at least a portion of a dataset.

Additionally, the input data for the different datasets can be varied or degraded to account for later variances in input data quality (e.g. 1 tesla or two tesla MRI) or type (e.g. CT scan or MRI scan). Datasets including different plans can be input with different types of imaging modalities or different qualities of image data input, as illustrated in FIG. 4. For example, a training dataset including a trajectory plan (wherein the trajectory plan can include an entry point 180, a target 230, and a path 182) can be input using MRI data 220 that was obtained with a one tesla MRI system. A substantially identical entry point, trajectory, and target for the same patient can also be input with image data acquired with a five tesla MRI system. Accordingly, a user can rate the substantially identical trajectory plan using image data both the one tesla MRI system and the five tesla MRI system to provide ratings for different qualities of image data to be used in the offline learning. It is understood that the rating can also include a plurality of rating metrics or measures. Exemplary rating metrics can include safety, efficacy side effect to a patient of the plan, expected surgical complexity and/or time, risk of damage to select anatomical or functional areas, and other appropriate or selected metrics. Each expert rater can rate each plan according to any and/or all of the selected metrics. Thus, each rated plan can include a combination of ratings for each of the metrics. Similarly, each plan that is identified or tested by the system can then be rated according to each of the metrics. Thus, an output can include a blended or composite rating (e.g. 8.2/10 overall) or a plurality of ratings where each rating is for one metric (e.g. safety=9.5/10; efficacy=3/10). Also, sub-sets of the metrics could be blended, such as a combination of safety and damage to selected areas can be blended while efficacy is left separate.

Once the different plans are rated, or after ratings and plans have been correlated or associated, the various trajectory plans (generally including the path, entry point, and target point) can be analyzed. Analysis of the plans can include various features as discussed herein. For example, shell modeling can be used to sample the image data along the trajectory in the selected dataset in block 116.

In shell sample data of the trajectories, the image data around the trajectory can be sampled by identifying a shell sample of trajectories substantially parallel to the trajectory in the selected dataset. Accordingly, it will be understood that sampling the image data in a shell model can be performed in each of the selected quantity of datasets inputted in block 112. In particular, it will be understood that the image data can be processed to identify various features of the trajectory in each of the selected datasets. Generally, each of the image data can be preprocessed using a median or selected low pass kernel. The image data can also be formatted and coordinated to align the image data along or with selected coordinates. For example, the AC and PC can be used to align the data within the selected datasets. A shell image can then be computed along the trajectory of the plan in the selected dataset.

Figure 5:
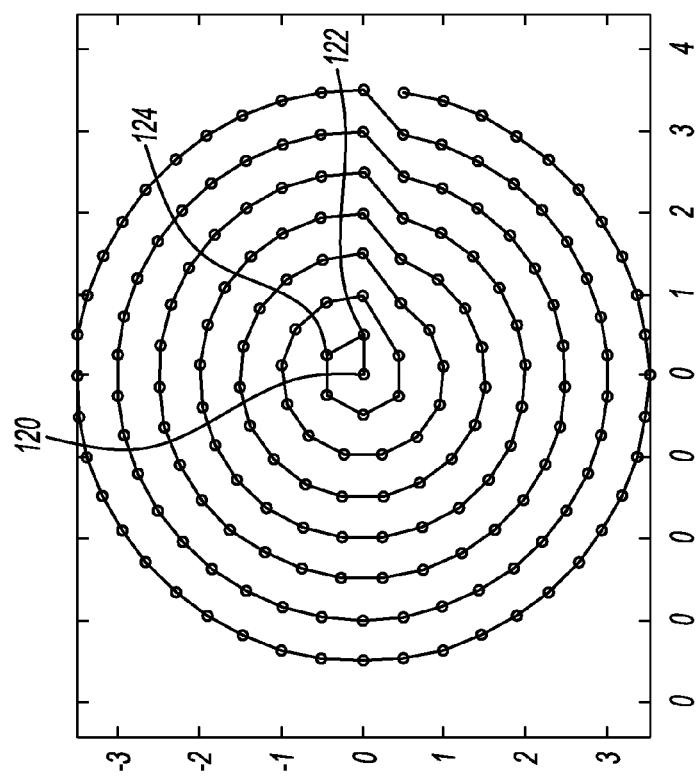
FIG. 5 is a diagram of a shell sample technique.

In generating the shell image, the image data can be sampled along the trajectory line between the target and the entry point within the image data. A shell sample can then be determined. As discussed briefly above, the shell sample can include determining a plurality of paths substantially parallel to the selected or determined trajectory within the selected dataset. As illustrated in FIG. 5, a shell sample can include a selected trajectory (e.g. an initial or input planned trajectory) that can be identified as a center trajectory 120. A selected plurality of other shell trajectories, such as a first shell trajectory 122 and a second shell trajectory 124, can be identified parallel to the first and generally pass through the image data at different points than the first trajectory 120. The shell sampling, by identifying a plurality of trajectories substantially parallel to the initial or planned trajectory 120, allows sampling the image data along trajectories other than the single trajectory of the plan to allow for sampling of data within the image data to create a greater sample than the single trajectory line. Further, it allows sampling a selected portion of the dataset substantially equivalent relative to the selected planned trajectory.

Once the shell sample has been determined, the intersection of the skin or other appropriate anatomical portion, such as the skull, can be determined within the image data using generally known edge or surface detection algorithms such as Sobel, Canny, or Zero-crossing. Detection can be based upon contrast or other appropriate edge detection to determine the skin surface or bone surface in the shell sample data. The image data can then be aligned based upon the determination of the skin or entry surface. The image data can then be sampled along the selected number of trajectories or shell trajectories.

Once the image data has been sampled into the shell data sample, the image data or the data relating to the shell sample can be normalized and/or compressed in block 130. Generally, it can be selected to normalize or compress the features of the sample data to minimize computational stresses and better correlate the variables that define the trajectories within the sample. Specific normalization or compression routines can include principal component analysis (PCA), independent component analysis (ICA), or two-dimensional discreet cosign transforms (2D-DCT). The various normalization or compression techniques can be used singly or in combination to compress or normalize the shell sample data for further analysis and use in learning algorithm. In particular, the dimensionality of the data can be reduced by performing selected transforms, such as the PCA. The normalized or compressed data can then be stored or used, either immediately or in further calculations, as discussed herein.

Geometric features of the trajectory can be measured or determined in block 140. The geometric configurations or features can be based upon the compressed or normalized data saved in block 130 or on the raw sample data obtained or determined in block 116. Nevertheless, geometric features can include the length of the trajectory or line from the entry point to the target point, angle calculations relative to the skin surface, planes of the anatomy, and geometric relations to known or identified structures. For example, structures can be identified in the image data (e.g. vasculature, commissure, sulci).

The identification of the structures can be based on automatic identification or by user identification. Nevertheless, the structures can be identified as either "good" or "bad". Good structures can include those structures that are preferred to be intersected with a selected trajectory. Bad structures can include those that are preferred to not be intersected or are selected to never be intersected with a trajectory. Accordingly, each of the structures identified in the image data can be weighted for use in the learning algorithm discussed further herein. In addition, the plan length can be used to identify a selected weight for use in the analysis of the learning algorithm as well. The angle or geometry of the trajectory can be calculated relative to the identified structures.

After the image data has been analyzed and sampled by a shell sample model in block 116, compressing or normalizing data in block 130 and measuring various geometric features of the trajectory in block 140, coefficients can be determined in block 150. The coefficients can any appropriate type of coefficients for use in the learning algorithm or as a part of the learning algorithm as discussed further herein.

The coefficients determined in block 150 can be a coefficient that is based upon various learning techniques such as linear regression, neural-network systems, genetic programming systems or other appropriate algorithm systems. Generally the learning algorithm can determine the coefficients that can be used to determined a rating for a selected trajectory. The different coefficients can be determined by achieving convergence or measuring convergence of the selected coefficient trajectory plans relative to the rated plans. The convergence can be based upon an absolute difference between the rating of the trajectories and the determined trajectories or a root mean square error between the determined plans or the correct or rated plans. The determined coefficients (i.e. learned coefficients) may then be used to rate plans based on different datasets (e.g. current subject datasets based on a subject for a current procedure to be performed).

A generated trajectory can be rated with the learned coefficients based upon the plurality of rated datasets originally input in block 112. Obtaining convergence of the predicted ratings allows for determining the learned or determined coefficients between the selected trajectories and the rated trajectories input in block 112. The learned or determined coefficient in block 150 can be saved in block 160. The saved coefficients can then be stored for later trajectory determination or rating based upon later input data, as discussed herein. The offline learning can end in block 162.

It will be understand, however, that the saved coefficients can be used to assist in rating or determining trajectories in a new or selected patient or operative patient dataset. Accordingly, with continuing reference to FIG. 3 and additional reference to FIG. 6, the saved coefficients can be used to rate trajectories according to a rating system 200. The rating system 200 can begin in block 202 after which operative patient data is input in block 204. A surgeon ID can optionally be put in block 206, as discussed above the learning algorithm can be specified for a particular user based upon the input surgeon ID in the learning algorithm. Accordingly, the saved coefficient inputs in block 160 can be correlated or determined for a particular surgeon (e.g. clinical user as discussed above), which can be recalled based upon the input of the surgeon ID in block 206.

After the optional input of the surgeon ID in block 206, a selected entry region or plurality of trajectories can be input in block 208. As illustrated in FIG. 7, an image or slice of a volume of the image 220 is illustrated. The image 220 can be image data of the selected patient input in block 204. As exemplary illustrated four entry points 222a-222d are illustrated as is a target 230. Additionally, four paths 232a-232d extend from each of the entry points 222a-222d to the target 230. Each of the entry points 222a-222d and the paths 232a-232d can be identified by the surgeon whose ID is input in block 206. Alternatively, the entry points 222a-222d in the respective paths 232a-232d can be generated automatically with a planning system or identified by another user. Regardless, a plurality of entry points and paths can be identified. Alternatively, or in additional thereto, a region (e.g. a surface area at an exterior of the patient) can be identified and one or more points within the region can be determined to be an entry point and trajectories can be determined from the entry point in the region to the target 230 by the system. Exemplary methods or systems for determining regions and possible trajectories from a point in a region to a target are can include those disclosed in U.S. patent application Ser. No. 12/103,488, published on Oct. 15, 2009 as U.S. Pat. App. Pub. 2009/0259230; Ser. No. 11/584,813, published on May 29, 2008 as U.S. Pat. App. Pub. 2008/0123922; Ser. No. 11/683,796, published on Apr. 3, 2008 as U.S. Pat. App. Pub. 2008/0081982; and Ser. No. 11/683,695, published on Mar. 13, 2008 as U.S. Pat. App. Pub. 2008/0064947; all incorporated herein by reference. In brief, a surface area or area relative to a patient can be identified as an entry region and a selected number or all possible trajectories from within the identified surface area to the target can be identified and analyzed.

Once the trajectories or regions are identified in block 208, a determination of patient specific features in the data input of the operative patient in block 204 can be performed in block 240. The determination of patient specific features can be similar to the sampling or image processing discussed in relation to the planning algorithm above. For example, the demographic or patient specific information (e.g. gender, age) can be identified or included in the data input. Additionally, the geometric features of the input trajectories or determined trajectories from the region can be determined. Also, specific image trajectory features can be identified, such as position relative to cautious zones (e.g. sulci) or selected passage zones can be identified. The data input in block 204 and the determination of patient specific features can then be normalized or compressed block 244.

The normalization or compression of the input data can include sampling within the shell around the selected or input trajectories, decreasing dimensionality of the data using various analyses (e.g. PCA) or other appropriate normalization or compression algorithms. Generally, it is selected to normalize the input data to substantially match the data used during the teaching of the learning algorithm as discussed in relation to the process illustrated in FIG. 3.

Once the data has been normalized or compressed in block 244, the saved coefficients can be recalled in block 246. The recalled coefficients can be the coefficients saved in block 160 illustrated in FIG. 3. Because the coefficients relate to correlation between the rated plans as input in the input dataset and in data that is substantially normalized or compressed similar to the normalizing in block 244, the input trajectories from block 208 can be rated based upon the recalled coefficients in block 246. Accordingly rating the input trajectories with the recalled coefficients can occur in block 250. The rating of the input trajectories can rate the input trajectories in block 208 or all of the trajectories from the specific region identified in block 208. Based upon the coefficients, ratings can be applied to the trajectories and ratings for the trajectories can be output in block 252. The output of ratings can be any appropriate output in block 252.

The output of the ratings can include a visual display, such as illustrated in block 252, that includes a chart or table 260 that illustrates ratings similar to ratings used in the learning discussed above. Alternatively, or in addition thereto, the rating number or value can be illustrated near to the trajectory lines 232a-232d. It will also be understood that other indicia including coloring of the lines 232a-232d based upon the rating determinations or other appropriate indicia. Alternately, or in addition thereto, only the highest rated trajectory can continue to be displayed or displayed on a display 502 (FIG. 9). Accordingly, the output rating of the trajectories in block 252 can include the display 502 illustrating only the image data 220 and the highest ranked trajectory or highest rated trajectory. The use or application of coefficient can end in block 280. Accordingly, the output rating of the trajectories in block 252 can be used by the surgeon to indentify or determine the ratings of the selected trajectories prior to performing a procedure. It will also be understood that the selection or rating can be done substantially intraoperatively to assist in determining an appropriate trajectory for performing a procedure. As discussed above and discussed further herein, placement of a DBS probe can be positioned within the brain of the patient 404 (FIG. 9) along a selected trajectory. By rating the trajectories in a substantially non-subjective manner with the learned coefficients (wherein the learned coefficients are based upon predetermined input regarding a plurality of similar procedures) the output of the rating of the trajectories in block 252 can include rating or input based upon a plurality of selected experts in addition to the individual clinician performing the procedure being presently planned. The output or the ratings can then be used to assist in performing a specific and/or current procedure, which can include navigating a DBS probe to a selected target 230, including the STN.

With reference to FIG. 8, an online or in-clinic learning or updating system 300 can also be provided, for example as discussed above online learning 18, 66. As discussed above, and illustrated in FIG. 1, both online and offline learning can be provided to determine the coefficients of the learning algorithm. Accordingly, offline learning can occur prior to or at any selected time to generate at least an initial set of learned coefficients. The learned coefficients can be based upon a selected set or number of datasets that can be updated once a system is provided or installed at a selected location. Accordingly, online learning can be understood to be updates or learning that occurs and updates the coefficients based upon a specific users input or additional training inputs. Accordingly, an example of online learning can include learning that occurs after a specific user obtains the system with the offline learned coefficients and provides additional inputs to the system to update the coefficients. Accordingly, the online method 300 can be used to update the coefficients used to rate the input plans or to define plans based on the input patient data.

The online learning 300 can start at block 302. A trajectory with image data can be presented in block 304. The presented trajectory can include a presentation such as that illustrated in FIG. 4 that illustrates the image data 220, with a training trajectory including the entry point 180, the target 230 and the training path 182. The training trajectory can be selected based upon an operative patient or any other patient or subject data. For example, the image data 220 can be a test case or historical data used for updating the coefficients. Nevertheless, once the trajectory is presented in block 304, the specific surgeon can rate the trajectory in block 306. Rating the trajectory can be a rating on the scale used the experts in the offline learning procedure. Accordingly, the online learning surgeon can rate the trajectory on the same scale as used by the selected expert raters when training the ATP system 14 during the offline learning procedure.

Once the trajectory is rated in block 306, the trajectory and image data can be sampled and processed similar to the offline learning. Accordingly, geometric considerations, placement, and other features in the imaged data, along with PCA scores or factors can be used to analyze the image data and the trajectory in block 308. Once the image data and the trajectory is sampled to be similar to the image data used and sampling of the trajectories in the offline learning procedure, the rating can be substantially correlated to the ratings of the offline procedure and the trajectory and the rating can then be used to update the coefficients in block 310. In updating the coefficients in block 310, the saved coefficients can be updated based upon the additional input by the surgeon by rating the trajectory in block 306. The updated coefficients can then be saved in block 312 and the online learning procedure can end in block 314. Accordingly, the online learning procedure allows the specific user or surgeon to provide specific inputs to the system to allow for customization of the coefficients to the specific surgeon. For example, a surgeon may preferably select a specific geometry or rate trajectories based upon positions relative to anatomical structures differently than other clinical experts. Accordingly, by providing the online learning and updating the coefficients in block 310, based upon ratings by specific surgeons or clinicians in block 306, the online learning can assist in learning specific coefficients for specific users or updating the coefficients from the offline learning to assist in providing substantially efficient and time efficient ratings based upon a specific surgeons input.

Using the online learning system 300 can allow a specific surgeon to update or rate trajectories. The updated coefficients can then be used by the specific surgeon, as suggested above, to rate a plurality of trajectories identified by the specific surgeon. The ratings for the specific trajectories can then be based more specifically on the specific users, or surgeons' inputs and desires. Accordingly, the rating system can be customized for a specific user and reduce the variance or difference between the rating of the trajectories and the specific users personal experience and expertise when determining trajectories to be used in a specific procedure.

The ATP system that is trained with the learning algorithm, discussed above, can be used as a rating system to be used in planning or assisting in performing a procedure. The performed procedure can be performed with a navigation system 400, as illustrated in FIG. 9. The ATP system can be incorporated into instructions that are executed by a planning processor system 500, discussed further herein, either as a separate processor system or incorporated in a processor system, such as a navigation processor 456. In any case, an instrument 446 can includes a DBS probe and can be navigated for performing a procedure. The selected procedure can be any appropriate procedure such as a DBS placement within a brain of the patient 404. It will be understood, however, that various instruments can be navigated along a selected or rated trajectories for various procedures such as placement of pedicle screws, guiding drug delivery stents or catheters, or other appropriate procedures. Regardless, and discussed further herein, the navigation system 400 can be used to assist in performing the procedure that is rated and/or selected based upon the ATP system.

FIG. 9 is a diagram illustrating an overview of a navigation system 400 that can be used for various procedures. The navigation system 400 can be used to track the location of an item, such as an implant or an instrument, and at least one imaging system 402 relative to a subject, such as a patient 404. It should be noted that the navigation system 400 may be used to navigate any type of instrument, implant, or delivery system, including: guide wires, arthroscopic systems, ablation instruments, stent placement, orthopedic implants, spinal implants, deep brain stimulation (DBS) probes, etc. Non-human or non-surgical procedures may also use the navigation system 400 to track a non-surgical or non-human intervention of the instrument or imaging device. Moreover, the instruments may be used to navigate or map any region of the body. The navigation system 400 and the various tracked items may be used in any appropriate procedure, such as one that is generally minimally invasive or an open procedure.

The navigation system 400 can interface with or integrally include an imaging system 402 that is used to acquire pre-operative, intra-operative, or post-operative, or real-time image data of the patient 404. It will be understood, however, that any appropriate subject can be imaged and any appropriate procedure may be performed relative to the subject. The navigation system 400 can be used to track various tracking devices, as discussed herein, to determine locations of the patient 404. The tracked locations of the patient 404 can be used to determine or select images for display to be used with the navigation system 400.

The imaging system 402 can comprise the O-Arm® imaging device sold by Medtronic Navigation, Inc. having a place of business in Louisville, Colo., USA. The second imaging device 402 includes imaging portions such as a generally annular gantry housing 410 that encloses an image capturing portion 412. The image capturing portion 412 may include an x-ray source or emission portion 414 and an x-ray receiving or image receiving portion 416. The emission portion 414 and the image receiving portion 416 are generally spaced about 180 degrees from each other and mounted on a rotor (not illustrated) relative to a track 418 of the image capturing portion 412. The image capturing portion 412 can be operable to rotate 360 degrees during image acquisition. The image capturing portion 412 may rotate around a central point or axis, allowing image data of the patient 410 to be acquired from multiple directions or in multiple planes.

The imaging system 402 can include those disclosed in U.S. Pat. Nos. 7,188,998; 7,108,421; 7,106,825; 7,001,045; and 6,940,941; all of which are incorporated herein by reference. The imaging system 402 can, however, generally relate to any imaging system that is operable to capture image data regarding the subject 404. The imaging system 402, for example, can include a C-arm fluoroscopic imaging system, magnetic resonance imagers, and computer tomography imagers which can also be used to generate three-dimensional views of the patient 404.

The patient 404 can be fixed onto an operating table 422, but is not required to be fixed to the table 422. The table 422 can include a plurality of straps 424. The straps 424 can be secured around the patient 404 to fix the patient 404 relative to the table 422. Various apparatuses may be used to position the patient 422 in a static position on the operating table 422. Examples of such patient positioning devices are set forth in commonly assigned U.S. patent application Ser. No. 10/405,068, published as U.S. Pat. App. Pub. No. 2004/0199072 on Oct. 7, 2004, entitled "An Integrated Electromagnetic Navigation and Patient Positioning Device", filed Apr. 1, 2003 which is hereby incorporated by reference. Other known apparatuses may include a Mayfield® clamp.

The navigation system 400 includes at least one tracking system. The tracking system can include at least one localizer. In one example, the tracking system can include an EM localizer 430, such as the EM localizer disclosed in U.S. Pat. App. Pub. No. 2004/019907 incorporated above and/or U.S. Pat. No. 7,751,865, incorporated herein by reference. The tracking system can be used to track instruments relative to the patient 404 or within a navigation space. The navigation system 400 can use image data from the imaging system 402 and information from the tracking system to illustrate locations of the tracked instruments, as discussed herein. The tracking system can also include a plurality of types of tracking systems including an optical localizer 432 in addition to and/or in place of the EM localizer 430. When the EM localizer 430 is used, the EM localizer can communicates with or through an EM controller 450. Communication with the EM controller can be wired or wireless.

The optical tracking localizer 432 and the EM localizer 430 can be used together to track multiple instruments or used together to redundantly track the same instrument. Various tracking devices, including those discussed further herein, can be tracked and the information can be used by the navigation system 400 to allow for an output system to output, such as a display device to display, a position of an item. Briefly, tracking devices, can include a patient or reference tracking device (to track the patient 404) 440, an imaging device tracking device 442 (to track the imaging device 402), and an instrument tracking device 444 (to track an instrument 446). The tracking devices allow selected portions of the operating theater to be tracked relative to one another with the appropriate tracking system, including the optical localizer 432 and/or the EM localizer 430. The reference tracking device 440 can be positioned within the patient 404 or on a surface or connected to a bone, such as a skull 448 of the patient 404

It will be understood that any of the tracking devices 440, 442, 444 can be optical or EM tracking devices, or both, depending upon the tracking localizer used to track the respective tracking devices. It will be further understood that any appropriate tracking system can be used with the navigation system 400. Alternative tracking systems can include radar tracking systems, acoustic tracking systems, ultrasound tracking systems, and the like. Each of the different tracking systems can have different and separate tracking devices and localizers operable with the respective tracking modalities. Also, the different tracking modalities can be used simultaneously as long as they do not interfere with each other (e.g. an opaque member blocks a camera view of the optical localizer 432).

An exemplarily EM tracking system can include the STEALTHSTATION® AXIEM™ Navigation System, sold by Medtronic Navigation, Inc. having a place of business in Louisville, Colo. Exemplary tracking systems are also disclosed in U.S. Pat. No. 7,751,865, issued Jul. 6, 2010 and entitled "METHOD AND APPARATUS FOR SURGICAL NAVIGATION"; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all incorporated herein by reference.

Further, for EM tracking systems it may be necessary to provide shielding or distortion compensation systems to shield or compensate for distortions in the EM field generated by the EM localizer 430. Exemplary shielding systems include those in U.S. Pat. No. 7,797,032, issued on Sep. 14, 2010 and U.S. Pat. No. 6,747,539, issued on Jun. 8, 2004; distortion compensation systems can include those disclosed in U.S. patent Ser. No. 10/649,214, filed on Jan. 9, 2004, published as U.S. Pat. App. Pub. No. 2004/0116803, all of which are incorporated herein by reference.

With an EM tracking system, the localizer 430 and the various tracking devices can communicate through an EM controller 450. The EM controller 450 can include various amplifiers, filters, electrical isolation, and other systems. The EM controller 450 can also control the coils of the localizer 430 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference, can be used as opposed to being coupled directly to the EM controller 450.

It will be understood that the tracking system may also be or include any appropriate tracking system, including a STEALTHSTATION® TRIA®, TREON®, and/or S7™ Navigation System having an optical localizer, similar to the optical localizer 432, sold by Medtronic Navigation, Inc. having a place of business in Louisville, Colo. Further alternative tracking systems are disclosed in U.S. Pat. No. 5,983,126, to Wittkampf et al. titled "Catheter Location System and Method," issued Nov. 9, 1999, which is hereby incorporated by reference. Other tracking systems include an acoustic, radiation, radar, etc. tracking or navigation systems.

The navigation system 400 can include or communicate with an image processing unit 454 that can be housed in a support housing or cart 452 of the imaging system 402. The cart 452 can be connected to the gantry 410. The navigation system 400 can also include a navigation processing system or unit 456 that can communicate or include a navigation memory from which image data, instructions, surgical plans (including trajectories), and other information can be recalled. The navigation processing unit 456 can include a processor (e.g. a computer processor) that executes instructions to determine locations of the tracking devices based on signals from the tracking devices. The navigation processing unit 456 can receive information, including image data, from the imaging system 402 and tracking information from the tracking systems, including the respective tracking devices and/or the localizers 430, 450. Image data can be displayed as an image 458 on a display device 460 of a workstation or other computer system 462 (e.g. laptop, desktop, tablet computer which may have a central processor to act as the navigation processing unit 456 by executing instructions). The computer system 462 can also include the navigation memory system. The workstation 462 can include appropriate input devices, such as a keyboard 464. It will be understood that other appropriate input devices can be included, such as a mouse, a foot pedal or the like which can be used separately or in combination. Also, all of the disclosed processing units or systems can be a single processor (e.g. a single central processing chip) that can execute different instructions to perform different tasks.

The image processing unit 454 can process image data from the imaging system 402. The image data from the image processor can then be transmitted to the navigation processor 456. It will be understood, however, that the imaging systems need not perform any image processing and the image data can be transmitted directly to the navigation processing unit 456. Accordingly, the navigation system 400 may include or operate with a single or multiple processing centers or units that can access single or multiple memory systems based upon system design.

In various embodiments, the position of the patient 404 relative to the imaging system 402 can be determined by the navigation system 400 with the patient tracking device 440 and the imaging system tracking device 442 to assist in registration. Accordingly, the position of the patient 404 relative to the imaging system 402 can be determined. Other registration techniques can also be used, including those generally known in the art to register a physical space defined relative to the patient 404 to image space defined by the image 458 displayed on the display device 460.

Manual or automatic registration can occur by matching fiducial points in image data with fiducial points on the patient 404. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in Ser. No. 12/400,273, filed on Mar. 9, 2009, now published as U.S. Pat. App. Pub. No. 2010/0228117, on Sep. 9, 2010, incorporated herein by reference.

Either provided with or operable to communicate with the navigation system is a planning system 500. The planning system 500 can include a computer processor (e.g. a central processing unit) to execute instructions based on the learning algorithm 14, 50. The learning algorithm can include the learned coefficients that are based on the training by the input of the selected experts in the offline learning 100 or the online learning 300.

The planning system 500 can be incorporated in a separate system, such as a separate portable computer system, or included in the processor system 462 discussed above. Regardless of the format, the planning system 500 is operable to execute instructions that are saved on an accessible memory to rate trajectories that are input or from within a region input. Accordingly, image data and other data of the operative patient 404 can be recalled or input into the planning system 500. The planning system 500, in executing the selected instructions of the ATP system 14, can rate the trajectories as in block 250 and then output the ratings as in block 252. In other words, the input patient data can be analyzed, as discussed above, and the learned coefficients can be used to rate or determine plans for a procedure. The output ratings can then be displayed on a display device 502 of the planning system 500 or on the display device 460.

The planning system 500 can also be used for the online training 300. The online training can be performed at a selected clinic and the planning system 500 can be used to allow the surgeon 18 to input personal or specific ratings. The surgeon 18 can input information or selections and ratings into the planning system 500 such as with a keyboard, computer mouse, etc.

The planning system 500, therefore, can be used to plan a procedure prior to bringing the patient 404 into the operative theater. Once trajectories are rated, the surgeon can select an appropriate trajectory, which includes an entry point and a path to the target. The image data can include the selected trajectory or the trajectory can be saved relative to a coordinate system of the image data. The image data and the related coordinates system can then be registered to the patient 404, as discussed above, once the patient 404 is moved into the operating theater. It will be understood, however, that the planning can occur while the patient 404 is in the operating theater, such as during operative preparation (e.g. operation site preparation, cleaning, etc.) rather than prior to moving the patient 404 into the operating theater. The procedure can be navigated using the navigation system 400 and using the selected trajectory.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of planning a trajectory to perform a procedure, comprising:
   selecting a plurality of training datasets regarding a plurality of training subjects, wherein each of the plurality of training datasets includes at least training image data;
   selecting at least one training trajectory in each of the selected plurality of training datasets;
   rating the at least one training trajectory in at least a selected sub-plurality of training datasets of the plurality of training datasets;
   executing instructions with a learning processor to process the training image data in each of at least the selected sub-plurality of training datasets of the plurality of training datasets;
   executing instructions with the learning processor to determine a learned rating coefficient that converges to a selected degree to predict the rating of each of the selected plurality of training trajectories;
   saving the determined learned rating coefficient;
   selecting a clinical dataset different from the plurality of training datasets including a clinical trajectory and a clinical image data;
   executing instructions with a clinical processor to process the clinical image data substantially similar to the instructions executed with the learning processor to process the training image data;
   executing instructions with the clinical processor to determine a clinical rating coefficient that converges to a selected degree to predict the rating of the clinical trajectory;
   determining a rating for the clinical trajectory based on the clinical rating coefficient.

2. The method of claim 1, wherein executing instructions with a learning processor to process the training image data includes sampling the training image data relative to the at least one training trajectory.

3. The method of claim 2, wherein executing instructions with a learning processor to process the training image data further includes reducing dimensionality of the sampled image data.

4. The method of claim 1, wherein executing instructions with the learning processor to determine rating coefficients includes executing a selected neural network algorithm to learn the rating of the selected at least one trajectory in each of the selected sub-plurality of the plurality of training datasets.

5. The method of claim 1, further comprising:
   selecting learning raters to rate the at least one training trajectory in at least the selected sub-plurality of training dataset of the plurality of training datasets;
   selecting a clinical rater to determine the clinical rating for the clinical trajectory;
   updating the saved learned coefficients with the determined clinical rating coefficient; and
   saving the updated learned coefficient.

6. The method of claim 5, further comprising:
   executing instructions with the clinical processor to rate a current subject trajectory based on a current subject dataset different from the plurality of training datasets with the saved updated learned coefficient.

7. A system to determine a trajectory to perform a procedure, comprising:
   a display device;
   an input device operable to allow an expert rater to input a rating of a trajectory;
   a learning processor operable to execute instructions to:
      display a training trajectory on the display device along with training image data;
      receive an input from the input device including a rating of the training trajectory;
      process the training image data at least to sample the image data in a shell relative to the training trajectory; and
      determine a coefficient relating the input rating and the displayed training trajectory;
   a memory device operable to store the saved coefficient;
   a current subject data input device operable to input current subject data and a current subject trajectory; and
   a rating processor operable to access the memory device including the saved coefficient and rate the current subject trajectory with the saved coefficient to determine a clinical rating coefficient that converges to a selected degree to predict the rating of the subject trajectory.

8. The system of claim 7, further comprising:
   an imaging device operable to acquire the image data.

9. The system of claim 7, wherein the learning processor and the rating processor are the same processor.

10. The system of claim 7, wherein process the training image data further includes reducing the dimensionality of the shell sampled data.

11. The system of claim 10, further comprising:
   a current subject data input device operable to input current subject data and a current subject trajectory different from the training trajectory;
   a rating processor operable to access the memory device including the saved coefficient and execute instructions to:
      process the current subject image data in a manner similar to the process training image data to generated current subject processed data and subsequently rate the current subject trajectory with the saved coefficient based on the processed current subject process data.

12. The system of claim 11, wherein determine the coefficient relating the input rating and the displayed training trajectory includes executing instructions for at least one of a linear regression, a neural-network, or a genetic programming system based at least on the input rating of the trajectory.

13. A method of planning a trajectory to perform a procedure, comprising:
   inputting a rating for at least one training trajectory in at least a selected sub-plurality of training datasets of a plurality of training datasets, wherein each of the plurality of training datasets includes at least training image data;
   executing instructions with a first processor to process the training image data in each of the selected sub-plurality of training datasets at least by sampling within a shell the training image data relative to the at least one training trajectory in the respective training dataset;
   executing instructions with a second processor to determine rating coefficient to predict the rating of each of the training trajectories based on the processed training image data and the input rating at least by determining a convergence of a selected coefficient for a selected training trajectory and the input rating for the selected training trajectory;

saving the determined rating coefficient;

inputting a current subject dataset different from the plurality of training datasets including at least one current subject trajectory;

executing instructions with the second processor to determine a current subject rating for the at least one current subject trajectory based on the saved coefficients such that the current subject rating converges to a selected degree to predict the rating of the at least one current subject trajectory; and outputting the current subject rating.

14. The method of claim 13, wherein executing instructions with the first processor to process the training image data further includes decreasing dimensionality of the data sampled in the shell.

15. The method of claim 14, wherein decreasing dimensionality of the data sampled in the shell includes projecting the shell sampled data into Principle Component Analysis space.

16. The method of claim 15, further comprising:

selecting a rating surgeon; and selecting a rating scale;

wherein inputting the rating includes the selected rating expert rating the at least one training trajectory based on the rating scale.

17. The method of claim 16, wherein selecting the rating surgeon includes selecting the rating surgeon to analyze the plurality of training datasets and at least one training trajectory in each training dataset of the plurality of training datasets based on prior knowledge of the selected rating surgeon.

18. The method of claim 16, further comprising:

processing the current subject dataset according to the processing of the training image datasets.

19. The method of claim 16, wherein the at least one current subject trajectory includes a plurality of current subject trajectories;

wherein executing instructions with the second processor to determine the current subject rating includes rating each current subject trajectory of the plurality of the current subject trajectories.

20. The method of claim 19, wherein the plurality of current subject trajectories are generated as at least a portion of all of the possible trajectories having an entry point with a selected area to reach a selected target.

21. The method of claim 16, wherein the plurality of training datasets regarding the plurality of subjects is acquired prior to the current subject dataset and are different from the current subject dataset;

wherein saving the determined rating coefficients includes saving the determined rating coefficients with a storage medium;

wherein executing instructions incorporating the saved coefficients to rate the at least one current subject trajectory includes recalling the determined rating coefficients.

22. The method of claim 13, wherein the first processor and the second processor are the same processor.

* * * * *